United States Patent [19]

Tarcsay et al.

[11] Patent Number: 4,971,802
[45] Date of Patent: Nov. 20, 1990

[54] LIPOSOMES OF SYNTHETIC LIPIDS

[75] Inventors: Lajos Tarcsay, Grenzach-Wyhlen; Hansjörg Eibl, Bovenden, both of Fed. Rep. of Germany; Peter Fankhauser, Ettingen; Anita Peil, Basel, both of Switzerland

[73] Assignee: Ciba-Geigy Corporation, Ardsley, N.Y.

[21] Appl. No.: 395,286

[22] Filed: Aug. 16, 1989

Related U.S. Application Data

[63] Continuation of Ser. No. 169,085, Mar. 17, 1988, abandoned, which is a continuation of Ser. No. 787,222, Oct. 15, 1985, abandoned.

[30] Foreign Application Priority Data

Oct. 16, 1984 [CH] Switzerland .................. 4951/84

[51] Int. Cl.$^5$ ............... A61K 9/127; A61K 37/22; A61K 45/05; B01J 13/02
[52] U.S. Cl. ............... 424/450; 264/4.1; 264/4.3; 264/4.6; 424/85.2; 424/85.5; 436/829; 514/885; 514/974; 428/402.2
[58] Field of Search ............ 264/4.1, 4.3, 4.6; 428/402.2; 424/85.5, 417, 450; 436/829; 514/885, 974

[56] References Cited

U.S. PATENT DOCUMENTS

| Re. 30,748 | 9/1981 | Sears | 260/403 |
|---|---|---|---|
| 4,302,459 | 11/1981 | Steck et al. | 514/313 |
| 4,406,890 | 9/1983 | Tarcsay et al. | 536/53 X |
| 4,427,649 | 1/1984 | Dingle et al. | 424/450 |
| 4,448,765 | 5/1984 | Ash et al. | 424/450 |
| 4,485,045 | 11/1984 | Regen | 428/402.2 |
| 4,515,736 | 5/1985 | Deamer | 264/4.3 |
| 4,619,794 | 10/1986 | Hauser | 264/4.1 |
| 4,622,219 | 11/1986 | Haynes | 514/818 X |
| 4,666,893 | 5/1987 | Tsuchiya | 514/78 |
| 4,673,567 | 6/1987 | Jizomoto | 264/4.3 X |
| 4,684,632 | 8/1987 | Schulz et al. | 514/78 |
| 4,774,085 | 9/1988 | Fidler | 424/85.5 |

FOREIGN PATENT DOCUMENTS

| 088946 | 9/1983 | European Pat. Off. . |
| 099068 | 1/1984 | European Pat. Off. . |
| 147741 | 7/1985 | European Pat. Off. . |
| 2647395 | 4/1978 | Fed. Rep. of Germany . |
| WO84/00367 | 2/1984 | PCT Int'l Appl. . |
| 1523965 | 9/1978 | United Kingdom . |

OTHER PUBLICATIONS

CS 200: 205314k (1984).
CA 89: 42466z (1978).

Primary Examiner—Richard D. Lovering
Attorney, Agent, or Firm—JoAnn Villamizar

[57] ABSTRACT

The invention relates to pharmaceutical compositions containing synthetic, substantially pure phosphatidyl serine and phosphatidyl choline and a substance or a mixture of substances having biological activity. The invention also relates to mixtures comprising synthetic, substantially pure phosphatidyl serine and phosphatidyl choline, and also to processes for the manufacture of the pharmaecutical compositions, and the use thereof.

10 Claims, No Drawings

LIPOSOMES OF SYNTHETIC LIPIDS

This application is a continuation of application Ser. No. 169,085, filed Mar. 17, 1988, and now abandoned, which is a continuation of Ser. No. 787,222, filed Oct. 15, 1985, now abandoned.

The present invention relates to pharmaceutical compositions containing synthetic, substantially pure phospholipids and a pharmaceutical active substance, mixtures of synthetic, substantially pure phospholipids, processes for the manufacture of these pharmaceutical compositions or mixtures, and the use thereof.

The pharmaceutical compositions according to the invention are used in the form of liposomes in aqueous dispersion.

Liposomes have been described in the literature in numerous publications. Many investigations are concerned with their structure and use. A distinction is made between unilamellar liposomes having a double layer of lipids and multilamellar liposomes having several double layers of lipids arranged in an onion skin-like manner.

There are suitable for pharmaceutical use especially liposomes having a population of as uniform a size as possible and a diameter of approximately from $2.0 \times 10^{-8}$ to $5.0 \times 10^{-6}$ m, preferably approximately from $2.0 \times 10^{-8}$ to $3.0 \times 10^{-6}$ m. The spherical shell consists of one or more double layers of lipid components, for example amphiphatic lipids, for example phospholipids, for example lecithin, cephalin or phosphatidic acid, and, optionally, neutral lipids, for example cholesterol. These double layers surround an interior space which contains an aqueous phase with a compound to be enclosed, it being possible for the compound to be enclosed to be present in the aqueous phase and/or in the double layer, depending upon the structure of the compound and other parameters, such as temperature or concentration.

There is a great deal of interest in the therapeutic use of liposomes as carriers for active substances of widely varied kinds. Accordingly, liposomes have been proposed as carriers for proteins, for example antibodies or enzymes, hormones, vitamins or genes or, for analytical purposes, as carriers for labelled compounds.

Pharmaceutical administration systems based on liposomes are described in the synoptical work of Gregoriadis, G. (editor) Liposome Technology, Vol. II, Incorporation of Drugs, Proteins and Genetic Material, CRC Press 1984. In the synoptical work of Knight, C. G. (editor), Liposomes: From Physical Structure to Therapeutic Applications, Elsevier 1981, the advantages of a pharmaceutical form of administration based on liposomes are summarised in chapter 16 on page 166:

1. Liposomes penetrate biological membranes and facilitate the transport of active substances through barriers that are normally impermeable. In particular, liposomes facilitate intracellular penetration by an encapsulated compound.

2. Liposomes can be used with a view to specific reciprocity with certain types of cell tissue, increased selectivity and reduced toxicity.

3. The pharmacokinetics of an active substance can be advantageously influenced by liposomes, for example by modifying the liberation, distribution and removal from the systemic circulation.

4. Active substances that are sensitive to changes caused by chemical influences and metabolism are protected by liposomes against deactivation.

5. Immunomodulating effects can be obtained by stimulating immune reactions of liposome-encapsulated antigens.

These result in further advantages, such as a reduction in the amounts of active substances required when using liposomes, as compared with using a free active substance, to achieve a therapeutic effect, or a reduction in the frequency of administration of the active substance.

Administration systems based on liposomes have special advantages when introducing substances into endocytising cells, especially of the reticuloendothelial system. There is observed, for example, a facilitation of the transport of antibiotics into endocytising cells and improved combating of the causative organisms present in those cells. Endocytising cells are also involved in inflammatory processes. A more rapid introduction of liposome-encapsulated antirheumatic active substances into such cells than into the surrounding tissue is observed Cytostatics encapsulated in the form of liposomes can be introduced into the specific organs of the reticuloendothelial system (liver, spleen, bone-marrow), or, in the lung, as a result of filtration in the lung capillaries and subsequent transport by emigrating blood monocytes, the active substances can be enriched in alveolar macrophages and it is therefore possible to achieve an improvement in the action on lung or liver tumours while at the same time reducing toxicity.

Liposomes having encapsulated immunomodulators can bring about a controlled change in the reactions of the immune system (immunostimulation, immunosuppression). For example, in Cancer Research 39, 881 (1979), Poste, G. et al. observe an activation of tumoricidal properties of mouse macrophages by liposome-encapsulated lymphokines. Sone, S. and I. J. Fidler, Cell. Immunol. 57, 42 (1981) report an in vitro activation of tumoricidal properties in alveolar rat macrophages by synthetic muramyl dipeptides encapsulated in liposomes.

Liposomes having immunomodulators, for example muramyl dipeptides and muramyl tripeptides, human gamma-interferon or macrophage-activating factor (MAF), are suitable for activating the cellular immune system, for example the cells of the monocytic system, for example blood monocytes or alveolar or peritoneal macrophages, for defense against infections, especially virus infections, and for combating tumour cells in primary tumour tissue in the blood and lymph, and for combating metastases.

The natural material used hitherto for the manufacture of liposomes, for example natural phospholipids, for example egg phosphatidic acid, egg or soya lecithin or egg or soya cephalin and bovine brain phosphatidyl serine, even if this material is in purified form and is supposed to be homogeneous according to thin-layer or paper chromatography, is a mixture of phosphoglycerides having acyl radicals of different structures. Dry preparations with natural phospholipids are thermolabile and will keep only for a short period and natural phospholipids in aqueous phase are also unstable so that aqueous liposome mixtures will likewise keep only for a limited period.

Because of the varying composition of liposome mixtures of natural phospholipids and because of the low yield, differing size distribution and their low degree of stability, in vitro and in vivo test results and clinical results lack the necessary reproducibility, which has hitherto had a restricting effect on the industrial usefulness of this form of administration which has been known for a relatively long time and on which intensive research has been carried out.

The problem of the present invention is to manufacture pharmaceutical compositions which, in aqueous phase, form liposome dispersions having a uniform size distribution and a high degree of stability.

The present invention relates to pharmaceutical compositions containing
(a) a synthetic, substantially pure phospholipid of the formula

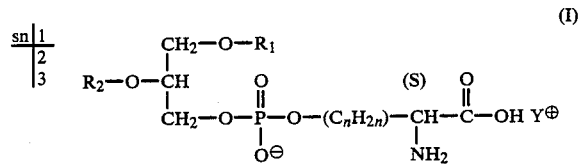

in which $R_1$ and $R_2$ each represents, independently of the other, $C_{10}$–$C_{20}$-alkenoyl having an even number of carbon atoms, n represents an integer from one to three and $Y^\oplus$ represents the cation of a pharmaceutically acceptable base,
(b) a synthetic, substantially pure phospholipid of the formula

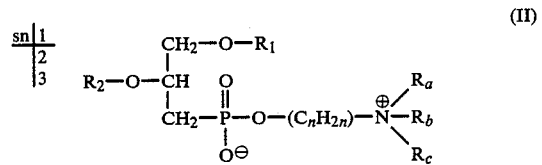

in which $R_1$ represents $C_{10}$–$C_{20}$-alkanoyl having an even number of carbon atoms, $R_2$ represents $C_{10}$–$C_{20}$-alkenoyl having an even number of carbon atoms, $R_a$, $R_b$ and $R_c$ represent hydrogen or $C_1$–$C_4$-alkyl and n represents an integer from two to four,
(c) a substance or a mixture of substances having biological activity and optionally a carrier liquid and/or additional solid carriers.

Within the ambit of the description of the present invention, the general terms mentioned hereinbefore and hereinafter preferably have the following meanings:

The term "lower" used in connection with organic radicals, for example lower alkyl, lower alkylene, lower alkoxy, lower alkanoyl, etc., means that such organic radicals, unless expressly defined otherwise, contain up to and including 7, and preferably up to and including 4, carbon atoms.

The nomenclature of the phospholipids of the formulae I and II is in accordance with the recommendations made in Eur. J. of Biochem. 79, 11–21 (1977) "Nomenclature of Lipids" by the IUPAC-IUB Commission on Biochemical Nomenclature (CBN) (sn nomenclature, stereospecific numbering).

Unless otherwise indicated, the generic names proposed by the World Health Organisation (WHO) (Recommended International Non-proprietary Names) are used for the pharmaceutical active substances and have been taken from the standard work "Pharmazeutische Chemie" (E. Schröder, C. Rufer and R. Schmiechen, Thieme Verlag Stuttgart, 1982) and from the Merck Index (Tenth Edition).

The purity of the synthetic phospholipids used is more than 90% by weight, preferably more than 95% by weight.

In a synthetic phospholipid of the formula I, $R_1$ and $R_2$ having the meaning "$C_{10}$–$C_{20}$-alkenoyl having an even number of carbon atoms" are preferably 9-cis-dodecenoyl, 9-cis-tetradecenoyl, 9-cis-hexadecenoyl, 6-cis-octadecenoyl, 6-trans-octadecenoyl, 9-cis-octadecenoyl, 9-trans-octadecenoyl, 11-cis-octadecenoyl or 9-cis-icosenoyl.

The cation $Y^\oplus$ of a pharmaceutically acceptable base is, for example, an alkali metal ion, for example the lithium, sodium or potassium ion, an ammonium ion, a mono-, di- or tri-$C_1$–$C_4$-alkylammonium ion, for example a trimethyl-, ethyl-, diethyl- or triethylammonium ion, a 2-hydroxyethyl-tri-$C_1$–$C_4$-alkylammonium ion, for example a choline cation, or a 2-hydroxyethylammonium ion, and the cation of a basic amino acid, for example lysine or arginine.

$Y^\oplus$ is preferably the sodium ion.

In a synthetic phospholipid of the formula I, $R_1$ and $R_2$ are preferably the same and represent 9-cis-dodecenoyl, 9-cis-tetradecenoyl, 9-cis-hexadecenoyl, 9-cis-octadecenoyl or 9-cis-icosenoyl, n is one and $Y^\oplus$ is the sodium ion.

A synthetic phospholipid of the formula I is especially sodium 1,2-di-(9-cis-octadecenoyl)-3- sn-phosphatidyl-(S)-serine.

In a synthetic phospholipid of the formula II, $R_1$ having the meaning "$C_{10}$–$C_{20}$-alkanoyl having an even number of carbon atoms" is preferably n-dodecanoyl, n-tetradecanoyl, n-hexadecanoyl, n-octadecanoyl or n-icosanoyl.

In a synthetic phospholipid of the formula II, $R_2$ has the meanings mentioned under formula I.

In a synthetic phospholipid of the formula II, the group of the formula—$(C_nH_{2n})$- is unbranched or branched alkylene, for example 1,1-ethylene, 1,1-, 1,2- or 1,3-propylene or 1,2-, 1,3- or 1,4-butylene, or preferably 1,2-ethylene (n=2).

In a synthetic phospholipid of the formula II preferably $R_1$ represents n-dodecanoyl, n-tetradecanoyl, n-hexadecanoyl or n-octadecanoyl, $R_2$ represents 9-cis-dodecenoyl, 9-cis-tetradecenoyl, 9-cis-hexadecenoyl, 9-cis-octadecenoyl or 9-cis-icosenoyl and $R_a$, $R_b$ and $R_c$ represent methyl and n is two.

A synthetic phospholipid of the formula II is especially 1-n-hexadecanoyl-2-(9-cis-octadecenoyl)-3-sn-phosphatidyl choline.

The names given in brackets are normally used for the acyl radicals $R_1$ and $R_2$ in the phospholipids of the formulae I and II:
9-cis-dodecenoyl (lauroleoyl), 9-cis-tetradecenoyl (myristoleoyl), 9-cis-hexadecenoyl (palmitoleoyl), 6-cis-octadecenoyl (petroseloyl), 6-transoctadecenoyl (petroselaidoyl), 9-cis-octadecenoyl (oleoyl), 9-trans-octadecenoyl (elaidoyl), 11-cis-octadecenoyl (vaccenoyl), 9-cis-icosenoyl (gadoleoyl), n-dodecanoyl (lauroyl), n-tetradecanoyl (myristoyl), n-hexadecanoyl (palmitoyl), n-octadecanoyl (stearoyl), n-icosanoyl (arachidoyl).

Substances or mixtures of substances having biological activity are especially pharmaceutical active substances and mixtures of substances from the groups comprising antiphlogistics, antibiotics, antileishmanias, antimycotics, antineoplastics and immunomodulators.

Pharmaceutical active substances from the group comprising antiphlogistics are, for example, glucocorticoids, for example cortisone, hydrocortisone, prednisone, prednisolone, fluocortolone, triamcinolone, methylprednisolone, prednylidene, paramethasone, dexamethasone, betamethasone, beclomethasone, fluprednylidene, desoxymethasone, fluocinolone, flumethasone, diflucortolone, clocortolone, clobetasol or fluocortin butyl ester, non-steroidal inflammation-inhibitors from the group comprising substituted phenylacetic acid salts or 2-phenylpropionic acid salts, for example alclofenac, ibufenac, ibuprofen, MK-830, BL-2365, clindanac, fenclorac, ketoprofen, fenoprofen, indoprofen, fenclofenac, diclofenac, flurbiprofen, pirprofen, naproxen, benoxaprofen, carprofen or cicloprofen, anthranilic acid derivatives, for example of the formula

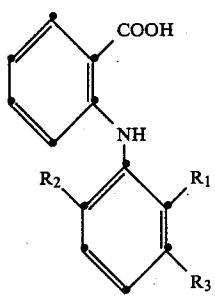 (III)

in which $R_1$, $R_2$ and $R_3$ each represents, independently of one another, hydrogen, methyl, chlorine or trifluoromethyl, for example mefenamic acid, flufenamic acid, tolfenamic acid or meclofenamic acid, anilino-substituted nicotinic acid derivatives, for example miflumic acid, clonixin or flunixin, heteroarylacetic acids or 2-heteroarylacetic acids having a 2-indol-3-yl or pyrrol-2-yl radical, for example indomethacin, oxmetacin, intrazol, acemetazin, cinmetacin, zomepirac, tolmetin, colpirac or tiaprofenic acid, an indenylacetic acid of the sulindac type and analgesically active heteroaryloxyacetic acids, for example benzadac.

Pharmaceutical active substances from the group comprising antibiotics are, for example, tetracycline antibiotics of the formula

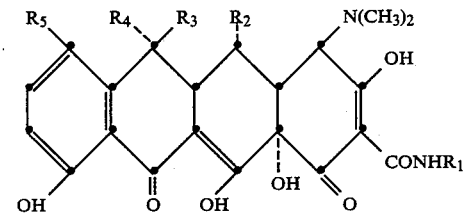 (V)

in which $R_1$ represents hydrogen or pyrrolidin-1-ylmethyl, $R_2$ represents hydrogen or hydroxy, $R_3$ represents hydrogen, hydroxy or methyl, $R_4$ represents hydrogen or methyl and $R_5$ represents hydrogen, chlorine or dimethylamino, for example chlortetracycline, oxytetracycline, tetracycline, demethylchlortetracycline, metacycline, doxycycline, minocycline or rolitetracycline, aminoglycosides, for example kanamycin, amikacin, gentamicin $C_{1a}$, $C_2$, $C_{2b}$ or $C_1$, sisomicin, netilmicin, spectinomycin, streptomycin, tobramycin, neomycin B, dibekacin or kanendomycin, macrolides, for example maridomycin or erythromycin, lincomycins, for example clindamycin or lincomycin, penicillanic acid (6-

APA)- and cephalosporanic acid (7-ACA)-derivatives having 6$\beta$- or 7$\beta$-acylamino groups, respectively, which are present in fermentatively, semi-synthetically or totally synthetically obtainable 6$\beta$-acylaminopenicillanic acid or 7$\beta$-acylaminocephalosporanic acid derivatives or 7$\beta$-acylaminocephalosporanic acid derivatives that are modified in the 3-position, for example penicillanic acid derivatives that have become known under the names penicillin G or V, phenethicillin, propicillin, nafcillin, oxacillin, cloxacillin, dicloxacillin, flucloxacillin, cyclacillin, epicillin, mecillinam, methicillin, azlocillin, sulbenicillin, ticarcillin, mezlocillin, piperacillin, carindacillin, azidocillin or ciclacillin, or cephalosporin derivatives that have become known under the names cefaclor, cefuroxime, cefazlur, cephacetrile, cefazolin, cephalexin, cefadroxil, cephaloglycin, cefoxitin, cephaloridine, cefsulodin, cefotiam, ceftazidine, cefonicid, cefotaxime, cefmenoxime, ceftizoxime, cephalothin, cephradine, cefamandol, cephanone, cephapirin, cefroxadin, cefatrizine, cefazedone, ceftrixon or ceforanid, and other $\beta$-lactam antibiotics of the clavam, penem or carbapenem type, for example moxalactam, clavulanic acid, nocardicine A, sulbactam, aztreonam or thienamycin, and antibiotics of the bicozamycin, novobiocin, chloramphenicol or thiamphenicol, rifampicin, fosfomycin, colistin or vancomycin type.

Pharmaceutical active substances from the group comprising antileishmanias are, for example, antimony compounds, for example tartar emetic (potassium antimonyl tartrate), stibophen, sodium stibocaptate and sodium stibogluconate.

Pharmaceutical active substances from the group comprising antimycotics are, for example, thiocarbonic acid derivatives, for example dibenzthione, tolnaftate or tolciclate, imidazole derivatives, for example clotrimazole, miconazole, econazole, isoconazole or ketoconazole or polyene antibiotics, for example nystatin, natamycin or amphotericin B.

Pharmaceutical active substances from the group comprising antineoplastics are, for example, alkylating agents having the bis-(2-chloroethyl)-amine group, for example chlormethine, chlorambucil, melphalan, uramustine, mannomustine, estramustine phosphate, mechlorethamine oxide, cyclophosphamide, ifosfamide or trifosfamide, alkylating agents having the aziridine structure, for example tretamine, thiotepa, triaziquone or mitomycin, alkylating methanesulphonic acid esters, for example busulphan, alkylating N-alkyl-N-nitrosourea derivatives, for example carmustine, lomustine, semustine or streptozotocin, and alkylating agents of the mitobronitol, dacarbazine or procarbazine type, antimetabolites of the folic acid type, for example methotrexate, purine derivatives, for example mercaptopurine, thioguanine, azathioprine, thiamiprine, vidarabine or puromycin, pyrimidine derivatives, for example fluorouracil, floxuridine, tegafur, cytarabine, idoxuridine, flucytosine, antibiotics that are used in cancer chemotherapy, for example dactinomycin, daunorubicin, doxorubicin, mithramycin, bleomycin $A_2$ or $B_2$ or etoposide, and vinca alkaloids, for example vincristine, optionally in combination with chlormethamine, prednisolone or prednisone and procarbazine.

Immunomodulators are, for example, muramyl peptides, for example muramyl dipeptides or muramyl tripeptides, especially of the formula (VI)

H₂N—Cys—Tyr—Cys—Gln—Asp—Pro—Tyr—Val—Lys—Glu—Ala—Glu—Asn—Leu—Lys—Lys—Tyr—
Phe—Asn—Ala—Gly—His—Ser—Asp—Val—Ala—Asp—Asn—Gly—Thr—Leu—Phe—Leu—Gly—Ile—
Leu—Lys—Asn—Trp—Lys—Glu—Glu—Ser—Asp—Arg—Lys—Ile—Met—Gln—Ser—Gln—Ile—Val—
Ser—Phe—Tyr—Phe—Lys—Leu—Phe—Lys—Asn—Phe—Lys—Asp—Asp—Gln—Ser—Ile—Gln—Lys—
Ser—Val—Glu—Thr—Ile—Lys—Glu—Asp—Met—Asn—Val—Lys—Phe—Phe—Asn—Ser—Asn—Lys—
Lys—Lys—Arg—Asp—Asp—Phe—Glu—Lys—Leu—Thr—Asn—Tyr—Ser—Val—Thr—Asp—Leu—Asn—
Val—Gln—Arg—Lys—Ala—Ile—His—Glu—Leu—Ile—Gln—Val—Met—Ala—Glu—Leu—Ser—Pro—
Ala—Ala—Lys—Thr—Gly—Lys—Arg—Lys—Arg—Ser—Gln—Met—Leu—Phe—Arg—Gly—Arg—Arg—
Ala—Ser—Gln—OH.

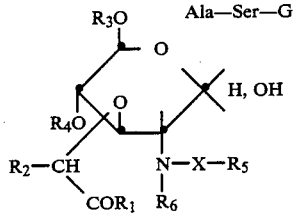

in which X represents the groups —C(=O)— or —C(=O)—O—, R₁ represents the L-Ala-D-isoGln-L-Ala-2-(1,2-dipalmitoyl-sn-glycero-3-hydroxyphosphoryloxy)-ethylamide group, the L-Ala-D-Glu(CY-L-Ala-2-(1,2-dipalmitoyl-sn-glycero-3-hydroxyphosphoryloxy)-ethylamide) group, the L-Ala-D-isoGlnOH group, the L-Ala-D-GlnNH₂-α-n-butyl ester group, the L-Ala-D-isoGln-L-(stearoyl)-Lys group, the L-Val-D-Gln-NH₂-α-n-methyl ester group, the L-Ala-D-isoGln-L-Ala-1,2-dipalmitoyl-sn-glycerine ester group or the L-Ala-D-isoGln-L-Ala-cholesterol ester group, R₂ represents hydrogen, methyl or n-propyl, R₃ represents hydrogen, n-stearoyl, 10-(2,3-dimethoxy-1,4-dioxo-5-methyl)-2,5-cyclohexadienoyl, 2-behenoyloxy-2-methylpropanoyl or n-octanoyl, R₄ represents hydrogen or n-octanoyl, R₅ represents C₁–C₄-alkyl and R₆ represents hydrogen or C₁–C₄-alkyl and the corresponding 2-palmitoylthio derivatives thereof, lipopeptides having immunomodulating properties of the n-lauroyl-L-Ala-D-isoGln-(m-DAP-Gly)-NH₂, n-lauroyl-L-Ala-D-isoGln-(L-DAP-Gly)-NH₂, n-lauroyl-L-Ala-D-isoGln-(L-Lys-D-Ala)-NH₂, n-octanoyl-L-Ala-D-isoGln-(L-Lys-D-Ala)-NH₂ or palmitoyl-Cys-((2R)-2,3-dilauroyloxypropyl)-Ala-D-Glu-(Gly-taurine-Na)-NH₂ type, or they are lymphokines that are secreted by lymphocytes, monocytes or macrophages when these are stimulated by antigens or mitogens or the like.

The group comprising lymphokines includes, for example, known types of interferon, especially natural or recombinant human gamma-interferon, for example human gamma-interferon which can be obtained in accordance with European Patent Applications Nos. 63,482, 77,670, 83,777, 88,540, 89,676, 95,350, 99,084, 110,044 and 112,967 and International Applications (PCT) WO 83/04,053 and WO 84/02,129.

Preferred is recombinant human gamma-interferon according to European Patent Application No. 121,157 having the following amino acid sequence:

and recombinant human gamma-interferon according to British Patent Application No. 2,107,718 having the following amino acid sequence:

The group comprising lymphokines also includes human interleukin 2 in purified form, for example interleukin 2 which can be obtained in the culture filtrate after activation of human neoplastic leukaemia or lymphoma cells by T-cell mitogens and which is purified by reverse phase HPLC, culture filtrates that can be obtained from cultures having human T-lymphocytes from the spleen or peripheral blood after stimulation by antigens or mitogens, for example human T-cell-leukaemia-lymphoma viruses (HTLV-I), phytohaemagglutinin or concanavalin A, and that contain mixtures that have components which have become known under the terms macrophage migration inhibition factor (MIF), leucocyte migration inhibition factor, leucocyte migration amplification factor, macrophage-activating factor (MAF), colony-stimulating factor, interleukin 1 and 2 and gamma-interferon, especially those culture filtrates or isolates having a high content of macrophage-activating factor (MAF).

The pharmaceutical compositions according to the invention are distinguished by a relatively uniform size (approximately $2.0-3.0\times 10^{-9}$ m) and good storage stability. For example, dry preparations (lyophilisates) consisting of the mentioned synthetic phospholipids and muramyl peptides will keep for a period varying from several months up to several years. The dry preparations can be dispersed very simply shortly before use in an aqueous buffer solution by shaking (Vortex) or vibration and can be used in situ, it being possible in most cases to avoid additional measures, such as filtration, neutralisation, dialysis, etc. Aqueous liposome dispersions having synthetic phospholipids and muramyl peptides as the inclusion compound will keep for a period varying from several weeks up to several months at temperatures below 10° C. and can even be rendered storage-stable in the form of a lyophilisate.

The pharmaceutical compositions according to the invention are distinguished by especially good physiological tolerance, for example low toxicity, and a favourable pharmacokinetic profile when they are administered in the form of an aqueous dispersion of liposomes. Thus, very rapid endocytosis takes place, especially through the cells of the monocytic system. Liposomes consisting of the mentioned synthetic phospholipids and a muramyl di- or tri-peptide as inclusion compound can H₂N—Cys—Tyr—Cys—Gln—Asp—Pro—Tyr—Val—Gln—Glu—Ala—Glu—Asn—Leu—Lys—Lys—
Tyr—Phe—Asn—Ala—Gly—His—Ser—Asp—Val—Ala—Asp—Asn—Gly—Thr—Leu—Phe—Leu—
Gly—Ile—Leu—Lys—Asn—Trp—Lys—Glu—Glu—Ser—Asp—Arg—Lys—Ile—Met—Gln—Ser—
Gln—Ile—Val—Ser—Phe—Tyr—Phe—Lys—Leu—Phe—Lys—Asn—Phe—Lys—Asp—Asp—Gln—
Ser—Ile—Gln—Lys—Ser—Val—Glu—Thr—Ile—Lys—Glu—Asp—Met—Asn—Val—Lys—Phe—
Phe—Asn—Ser—Asn—Lys—Lys—Lys—Arg—Asp—Asp—Phe—Glu—Lys—Leu—Thr—Asn—Tyr—
Ser—Val—Thr—Asp—Leu—Asn—Val—Gln—Arg—Lys—Ala—Ile—His—Glu—Leu—Ile—Gln—
Val—Met—Ala—Glu—Leu—Ser—Pro—Ala—Ala—Lys—Thr—Glu—Lys—Arg—Lys—Arg—Ser—
Gln—Met—Leu—Phe—Gln—Gly—Arg—Arg—Ala—Ser—Gln—OH.

be enriched particularly well in the lung and liver and are rapidly endocytised by macrophages. In particular, alveolar macrophages are stimulated and physiologically abnormal materials, for example viruses or metastasising tumour cells, are eliminated. The pharmaceutical compositions according to the invention in the form of liposomes are therefore extremely suitable in cancer chemotherapy for combating metastasising tumours The mixture of phospholipids (I) and (II) which can be used for the manufacture of the pharmaceutical compositions according to the invention has, after dispersion in aqueous phase, a phase transition temperature (liquid-gel form) of less than approximately 37° C. The liposome dispersion can be manufactured without heating.

Aqueous dispersions in which the phospholipids of the formulae I and II are in the form of liposomes in which the mentioned compounds or substance mixtures having biological activity are enclosed are pharmaceutical administration systems which, optionally after concentration or isolation of the liposomes, for example by ultracentrifugation, are suitable for therapeutic purposes for oral (p.o.) or parenteral (i.v., i.m., i.p. or topical) administration.

In the case of oral administration, administration systems based on liposomes can improve the absorption of an active ingredient.

For oral administration, the liposome-containing aqueous dispersion, buffered to pH 7.0–7.8, preferably 7.2–7.4, can be mixed with pharmaceutically acceptable diluents or carriers or with customary additives, for example colourings or flavourings, and can be used in the form of a syrup or in the form of capsules.

For parenteral administration, the liposomes are dispersed in a sterile aqueous solution which serves as a carrier liquid, for example sterile, calcium-free, isotonic saline or glucose solution, buffered to pH 7.0–7.8, preferably 7.2–7.4.

For topical administration, the liposome-containing aqueous dispersion, buffered to pH 7.0–7.8, preferably 7.2–7.4, is mixed, with customary solid carriers, for example thickeners, for example hydroxypropylcellulose, and suitable preservatives, antioxidants or perfumes and used in the form of a lotion or gel for application to the skin or the mucous membranes.

The invention relates in a narrower sense to pharmaceutical compositions containing synthetic, substantially pure phospholipids in a mixing ratio of phospholipids of the formula I to phospholipids of the formula II of from approximately 10:90 to approximately 50:50 mol %, and a pharmaceutical active substance or a mixture of substances from the groups comprising antiphlogistics, antibiotics, antileishmanias, antimycotics, antineoplastics and immunomodulators, and optionally a carrier liquid buffered to pH 7.0–7.8 and/or additional solid carriers.

The invention relates preferably to pharmaceutical compositions containing (a) a synthetic, substantially pure phospholipid of the formula I in which $R_1$ and $R_2$ are the same and represent 9-cis-dodecenoyl, 9-cis-tetradecenoyl, 9-cis-hexadecenoyl, 9-cis-octadecenoyl or 9-cis-icosenoyl, n is one and $Y^\oplus$ is the sodium ion, (b) a synthetic, substantially pure phospholipid of the formula II in which $R_1$ represents n-dodecanoyl, n-tetradecanoyl, n-hexadecanoyl or n-octadecanoyl, $R_2$ represents 9-cis-dodecenoyl, 9-cis-tetradecenoyl, 9-cis-hexadecenoyl, 9-cis-octadecenoyl or 9-cis-icosenoyl and $R_a$, $R_b$ and $R_c$ represent methyl, (c) a pharmaceutically active substance or a mixture of substances from the groups comprising antiphlogistics, antibiotics, antileishmanias, antimycotics, antineoplastics and immunomodulators, and optionally a carrier liquid buffered to pH 7.2–7.4.

The invention relates especially to pharmaceutical compositions containing (a) synthetic, substantially pure sodium 1,2-di-(9-cis-octadecenoyl)-3-sn-phosphatidyl-(S)-serine, (b) synthetic, substantially pure 1-n-hexadecanoyl-2-(9-cis-octadecenoyl)-3-sn-phosphatidyl choline, (c) a pharmaceutically active substance or a mixture of substances from the groups comprising antiphlogistics, antibiotics, antileishmanias, antimycotics, antineoplastics and immunomodulators, and optionally a carrier liquid buffered to pH 7.2–7.4.

The invention relates more especially to pharmaceutical compositions containing (a) synthetic, substantially pure sodium 1,2-di-(9-cis-octadecenoyl)-3-sn-phosphatidyl-(S)-serine, (b) synthetic, substantially pure 1-n-hexadecanoyl-2-(9-cis-octadecenoyl)-3-sn-phosphatidyl choline, (c) a pharmaceutically active substance or a mixture of substances from the groups comprising antiphlogistics, for example diclofenac or pirprofen, antineoplastics, for example mitomycin, cytarabine, dactinomycin, daunorubicin, doxorubicin or etoposide, immunomodulators, for example N-acetylmuramyl-L-alanyl-D-isoglutaminyl-L-alanine-2-(1,2-dipalmitoyl-sn-glycero-3-hydroxyphosphoryloxy) -ethylamide, the disodium salt of N-acetylmuramyl-L-alanyl-D-glutamic acid-($C_\gamma$)-L-alanine-2-(1,2-dipalmitoyl-sn-glycero-3-hydroxyphosphoryloxy) -ethylamide, the sodium salt of N-acetyldesmethylmuramyl-L-alanyl-D-isoglutamine, the sodium salt of N-acetyl-D-muramyl-L-alanyl-D-isoglutamine, N-acetyl-D-muramyl-L-alanyl-D-glutamine-$\alpha$-n-butyl ester, $N^\alpha$-(N-acetyl-D-muramyl-L-alanyl-D-isoglutaminyl)-$N^\epsilon$-stearoyl-L-lysine or 6-0-stearoyl-N-acetylmuramyl-L-alanine-D-isoglutamine, lymphokines or combinations thereof, and optionally a carrier liquid buffered to pH 7.2–7.4.

The invention relates more especially to pharmaceutical compositions containing (a) synthetic, substantially pure sodium 1,2-di-(9-cis-octadecenoyl)-3-sn-phosphatidyl-(S)-serine, (b) synthetic, substantially pure 1-n-hexadecanoyl-2-(9-cis-octadecenoyl)-3-sn-phosphatidyl choline, (c) a pharmaceutically active substance from the groups comprising antineoplastics, for example mitomycin, cytarabine, dactinomycin, daunorubicin, doxorubicin or etoposide, and immunomodulators, for example N-acetylmuramyl-L-alanyl-D-isoglutaminyl-L-alanine-2-(1,2- dipalmitoyl-sn-glycero-3-hydroxyphosphoryloxy)-ethylamide, the sodium salt of N-acetyldesmethylmuramyl-L-alanyl-D-isoglutamine, the sodium salt of N-acetyl-D-muramyl-L-alanyl-D-isoglutamine or lymphokines, for example human gamma-interferon or interleukin 2 or mixtures of substances that are contained in culture filtrates obtained from cultures having human T-lymphocytes from the spleen or peripheral blood after stimulation by antigens or mitogens and that are characterised by a high content of macrophage-activating factor (MAF), or combinations thereof, and optionally a carrier liquid buffered to pH 7.2–7.4.

The invention relates first and foremost to pharmaceutical compositions containing (a) synthetic, substantially pure sodium 1,2-di-(9-cis-octadecenoyl)-3-sn-phosphatidyl-(S)-serine, (b) synthetic, substantially pure 1-n-hexadecanoyl-2-(9-cis-octadecenoyl)-3-sn-phosphatidyl choline, (c) a compound having immunomodulating action, for example N-acetylmuramyl-L-alanyl-D-isoglutaminyl-L-alanine-2-(1,2-dipalmitoyl-sn-glycero-3-hydroxyphosphoryloxy) -ethylamide, the sodium salt of N-acetyldesmethylmuramyl-L-alanyl-D-isoglutamine or the sodium salt of N-acetyl-D-muramyl-L-alanyl-D-isoglutamine, optionally in combination with mixtures of substances that are contained in culture filtrates obtained from cultures having human T-lymphocytes from the spleen or peripheral blood after stimulation by antigens or mitogens and that are characterised by at least a 70% content of MAF, and optionally a carrier liquid buffered to pH 7.2–7.4.

The mentioned pharmaceutical compositions can be marketed in the form of dry preparations and can be used in the form of an aqueous liposome dispersion in a carrier liquid buffered to pH 7.0–7.8.

The dosage of the active substance to be administered is generally the highest and lowest amount prescribed, for example in the Deutsches Arzneimittelbuch (DAB) [German Pharmacopoeia], and known for the active substance in question for the particular form of administration, the age of the patient and the health of the patient. Aqueous dispersions with liposomes that can be manufactured according to the invention also have the advantage, however, that active substances administered in smaller doses can pass to the receptors and can there bring about a therapeutic effect, or, on administration of higher doses, undesirable side effects can be avoided The preferred dosage of the mentioned immunomodulators of the muramyl peptide or lipopeptide type, which are encapsulated in the form of liposomes, is from 0.01 to approximately 10 mg/kg body weight per
administration. In the case of lymphokines in liposome form, for example human gamma-interferon or mixtures containing MAF, the preferred dosage is approximately from 100 to 100,000 units/ml gamma-interferon or MAF.

The invention also relates to mixtures, especially homogeneous mixtures of synthetic, substantially pure phospholipids of the formulae I and II, especially mixtures in a mixing ratio of phospholipids of the formula I to phospholipids of the formula II from approximately 10:90 to approximately 50:50 mol %. A mixing ratio of 30:70 mol % is preferred. These mixtures can be used for the manufacture of liposomes in an aqueous phase containing a water-soluble active substance.

The pharmaceutical compositions according to the invention or the mentioned mixtures are manufactured, for example, as follows:

(a) a homogeneous mixture comprising synthetic, substantially pure phospholipids of the formulae I and II and a lipophilic substance or mixture of substances having biological activity is manufactured and, for the manufacture of liposomes, the resulting homogeneous mixture is dispersed in an aqueous phase, or (b) a homogeneous mixture comprising synthetic, substantially pure phospholipids of the formulae I and II is manufactured and, for the manufacture of liposomes, the resulting homogeneous mixture is dispersed in an aqueous phase containing a water-soluble substance or mixture of substances having biological activity, and, if necessary, the resulting aqueous dispersion is buffered to pH 7.0–7.8 and, if desired, the resulting liposomes are enriched and/or separated off.

The homogeneous mixture is manufactured, for example, by film formation or preferably by lyophilisate formation.

The film formation is carried out according to process variant (a) by dissolving the synthetic phospholipids of the formulae I and II and the lipophilic substance or mixture of substances to be encapsulated, or according to process variant (b) by dissolving the synthetic phospholipids of the formulae I and II in an organic solvent having a low melting point and removing the solvent.

The choice of suitable solvents for the manufacture of a film is dependent on the solubility of the lipid components and the inclusion compounds. Suitable solvents for the manufacture of the homogeneous mixture by film formation are, for example, low-boiling and low-melting (below 0° C.), unsubstituted or substituted, for example halogenated, hexane, cyclohexane, methylene chloride or chloroform, alcohols, for example methanol, lower alkanecarboxylic acid esters, for example ethyl acetate, or ethers, for example diethyl ether, or mixtures of these solvents. The solvent is removed in vacuo, preferably under a high vacuum, or by blowing off with an inert gas, for example nitrogen.

The lyophilisate formation is carried out according to process variant (a) by lyophilising a solution of the synthetic phospholipids of the formulae I and II and the lipophilic substance or mixture of substances to be encapsulated, or according to process variant (b) by lyophilising a solution of the synthetic phospholipids of the formulae I and II in an organic solvent having a high melting point in the manner described in DE-A-2,818,655. Suitable solvents are solid during freeze-drying, for example at the temperature of a methanol-, ethanol- or acetone-dry ice mixture, together with the lipid components and the inclusion compounds, and are, for example, organic solvents having a melting point higher than 0° C., for example glacial acetic acid, benzene or dioxan, especially tert.-butanol.

A homogeneous mixture can also be manufactured by spray-drying a solution of the phospholipids and the lipophilic inclusion compounds in an organic solvent, for example chloroform. The homogeneous mixture is obtained in the form of a powder.

An approximate mixing ratio of phospholipids of the formula I to phospholipids of the formula II from approximately 10:90 to approximately 50:50 mol %, especially 30:70 mol %, is suitable for the manufacture of the homogeneous mixture. The approximate mixing ratio of the inclusion compounds to the total amount of lipids is approximately from 0.001 to 1.0:1.0, preferably from 0.005 to 0.1:1.0 mol.

Dispersion is effected, for example, by shaking (for example Vortex mixer) or stirring the aqueous phase to which has been added, according to process variant (a), the previously manufactured homogeneous mixture of the phospholipids (I) and (II) and the lipophilic inclusion compounds, or which, according to process variant (b), contains the water-soluble inclusion compound and to which has been added the previously manufactured homogeneous mixture of phospholipids (I) and (II). The formation of liposomes, which may be large, small, unilamellar or multilamellar, takes place spontaneously (spontaneous vesiculation), that is to say without the additional supply of external energy and at high speed. Approximately from 0.1 to 50% by weight, preferably from 2 to 20% by weight (in relation to the total weight of the aqueous dispersion) of the homogeneous mixture can be dispersed in the aqueous phase.

Acidically or basically reacting aqueous dispersions are buffered to pH 7.0–7.8, preferably pH 7.2–7.4. Dispersion is preferably carried out in an aqueous phase that has already been buffered to that pH value.

Process variant (a) is especially suitable when lipophilic and sparingly water-soluble active substances are to be enclosed in the form of liposomes, for example muramyl di- or tri-peptides. Process variant (b) is indicated when a liposome mixture of water-soluble active substances, for example cytarabine or cytostatics of the trifosfamide type, is to be manufactured.

The manufacture of the pharmaceutical compositions according to the invention in the form of aqueous liposome mixtures can also be carried out according to any of the other processes that have become known hitherto for the manufacture of liposomes, for example in customary manner by treating the aqueous dispersion containing the phospholipids (I) and (II) and the inclusion compounds with ultrasonic waves, or by infusion methods or reverse-phase evaporation.

Dispersion is carried out at temperatures below approximately 36° C., preferably at room temperature. If the sensitivity of the compounds to be encapsulated demands, the process is carried out while cooling and optionally under an inert gas atmosphere, for example a nitrogen or argon atmosphere. The resulting liposomes are stable for a very long period (up to several weeks or months) in an aqueous phase. Pharmaceutical compositions in the form of aqueous liposome dispersions can, optionally after the addition of stabilisers, for example mannitol or lactose, be rendered storage-stable by freeze-drying.

The size of the unilamellar liposomes formed depends, inter alia, on the structure of the active substance and the lipid components, the mixing ratio of the components and the concentration of those components in the aqueous dispersion. For example, by increasing or decreasing the concentration of the lipid components, it is possible to manufacture aqueous phases having a high content of small or large liposomes.

By after-treatment of the liposome dispersion, for example by treatment with ultrasonic waves or by extrusion through straight-pored filters (for example Nucleopore ®), it is possible to obtain an especially uniform size distribution of the liposomes.

The separation of the large liposomes from the small liposomes, if actually necessary, is carried out by means of customary separation methods, for example gel filtration, for example using Sepharose 4B or Sephacryl as carrier, or by sedimentation of the liposomes in an ultracentrifuge, for example at 160,000×g. For example, after several hours', for example approximately three hours', centrifugation in that gravitational field large liposomes are deposited while the small liposomes remain dispersed and can be decanted off. After several hours' centrifugation, complete separation of the large from the small liposomes is achieved.

Liposomes are preferably separated off if, according to process variant b), the aqueous phase contains nonencapsulated water-soluble compounds. In particular, water-soluble antineoplastics, for example alkylating agents, should be separated off, for example by filtration, ultrafiltration, dialysis or centrifugation, since these active substances are not tolerated particularly well in dissolved form. The enriched liposomes can be mixed with a carrier liquid, for example isotonic sterile saline solution. Aqueous dispersions having small liposomes of relatively uniform size are also obtained by ultrasound treatment.

It is also possible to separate off all the liposomes in the aqueous phase having a diameter greater than $6.0 \times 10^{-8}$ m and also non-encapsulated lipophilic active substances and excess dispersed lipids that are present in high-molecular-weight aggregates, by gel filtration and thus to obtain an aqueous dispersion having a fraction of liposomes of relatively uniform size.

The completed formation of liposomes and their content in the aqueous phase can be detected in a manner known per se using various physical measuring methods, for example with freeze fracture samples and thin sections in an electron microscope or by X-ray diffraction, by dynamic light scattering, by mass determination of the filtrate in an analytical ultracentrifuge and especially by spectroscopy, for example in the nuclear resonance spectrum ($^1$H, $^{13}$C and $^{31}$P).

Synthetic, substantially pure phospholipids of the formulae I and II are known. For example, Browning J. and Seelig J., in the synoptical article "Synthesis of Specifically Deuterated Saturated and Unsaturated Phosphatidylserins" in Chem. and Physics of Lipids 24 (1979), 103–118, describe the manufacture of 1,2-di-(9-cis-octadecenoyl)-3-sn-phosphatidyl-(S)-serine.

The pharmaceutical active substances from the groups comprising antiphlogistics, antibiotics, antileishmanias and cancer chemotherapeutic agents are known, see Merck Index, Tenth Edition, or the above-mentioned synoptical work of Schröder et al. "Pharmazeutische Chemie".

The mentioned immunomodulators of the muramyl peptide type of the formula VI are also known, see, for example, European Patent Specifications Nos. 25495 and 21367 and French Patent Specification No. 7,637,091.

The mentioned immunomodulators of the lipopeptide type are also known, see, for example EP-A-114,787 or European Patent Specification No. 330

The manufacture of purified interleukin 2 is described in EP-A-0106179 and in U.S. Pat. No. 4,448,879.

Mixtures of substances containing macrophage migration inhibition factor (MIF), leucocyte migration inhibition factor, leucocyte migration amplification factor, macrophage-activating factor (MAF), colony-stimulating factor, etc., have been described in numerous publications, for example Salahuddi S. Z. et al. Science 223 (4637) 703–707 (1984). The manufacture of culture filtrates having an especially high content of human MAF has also been described in numerous publications, for example Le J. et al. J. Immunology, Vbl. 131, 2821–2826 (1983), Kleinermann et al., J. Clinical Investigation, 72, 304–315 (1983), Cameron D. J., J. Clin. Lab. Immunol. (1984), 13, 47–50, and Kleinermann E. S. and Fidler I. J., Lymphokine Research, Vol. 2, No. 1, 7–12 (1983).

The buffer solutions used, having a pH of 7.0 to 7.8, are preferably sterile phosphate buffer solutions based on dihydrogen/hydrogen phosphate which can be manufactured, for example, in accordance with the instructions given in Hagers Handbuch der Pharmazeutischen Praxis, Springer Verlag, Volume 1, pages 357–359. Use is made especially of sterile isotonic calcium-free buffer solution having a pH of 7.2 (Dulbecco).

The following Examples illustrate the invention without limiting it. Temperatures are given in degrees Centigrade.

EXAMPLE 1

586 mg of sterile tert.-butanol, 0.1 mg of N-acetylmuramyl-L-alanyl-D-isoglutaminyl-L-alanine-2 -(1,2-dipalmitoyl-sn-glycero-3-hydroxyphosphoryloxy)ethylamide (manufactured according to European Patent Specification 25 495), 75 mg of (95% pure) sodium 1,2-di-(9-cis-octadecenoyl)-3-sn-phosphatidyl-(S)-serine (manufactured according to Browning J. and Seelig J., Chem. and Physics of Lipids 24 (1979) 103–118) and 175 mg of (95% pure) 1-n-hexadecanoyl-2-(9-cis-octadecenoyl)-3-sn-phosphatidyl choline (Avanti, Polar Lipids) are dissolved in a round-bottomed flask. The solution is sterile-filtered over Acrodisc ($2.0 \times 10^{-7}$ m), introduced into a sterile phial and frozen at $-45°$. The phial is dried in vacuo until a temperature of 25° is reached, and sealed under an argon atmosphere.

Before use, 2.5 ml of sterile, calcium-free, phosphate-buffered (pH 7.2–7.4) saline solution (Dulbecco) are added to this dry preparation (lyophilisate) at room temperature, using a sterile syringe, and the phial is shaken for ten minutes in a standardised laboratory shaking apparatus (Vortex, stage 6). The resulting liposome dispersion is storable at 4° and is suitable for parenteral (i.v.) administration.

EXAMPLE 2

586 mg of sterile tert.-butanol, 0.1 mg of N-acetylmuramyl-L-alanyl-D-isoglutaminyl-L-alanine-2-(1,2-dipalmitoyl-sn-glycero-3-hydroxyphosphoryloxy)ethylamide (manufactured according to European Patent Specification 25 495), 75 mg of (95% pure) sodium 1,2-di-(9-cis-octadecenoyl)-3-sn-phosphatidyl-(S)-serine (manufactured according to Browning J. and Seelig J., Chem. and Physics of Lipids 25 (1979) 103–118) and 175 mg of (95% pure) 1-n-hexadecanoyl-2-(9-cis-octadecenoyl) -3-sn-phosphatidyl choline (Avanti, Polar Lipids) are dissolved in a round-bottomed flask. The solution is sterile-filtered over Acrodisc ($2.0 \times 10^{-7}$m) and introduced into a sterile phial. The phial is rotated at 150 rpm and the solvent is removed by blowing in a stream of purified nitrogen that has been filtered under a pressure of 1 bar. The phial is then evacuated under a high vacuum of $6.0 \times 10^{-2}$ mbar. The phial is sealed under an argon protecting-gas atmosphere.

Before use, 2.5 ml of sterile, calcium-free, phosphate-buffered (pH 7.2–7.4) saline solution (Dulbecco) are added at room temperature, using a sterile syringe, to the film that has been manufactured, and the phial is shaken for ten minutes in a standardised laboratory shaking apparatus (Vortex, stage 6). The resulting liposome dispersion is storable at 4° and is suitable for parenteral (i.v.) administration.

EXAMPLE 3

Aqueous dispersions containing liposomes consisting of 75 mg (0.091 mmol) of sodium 1,2-di-(9-cis-octadecenoyl)-3-sn-phosphatidyl serine, 175 mg (0.231 mmol) of 1-n-hexadecanoyl-2-(9-cis-octadecenoyl)-3-sn-phosphatidyl choline and from more than 0.1 mg up to 10 mg of N-acetylmuramyl-L-alanyl-D-isoglutaminyl-L-alanine-2-(1,2-dipalmitoyl-sn-glycero-3-hydroxyphosphoryloxy)-ethylamide can be manufactured in a manner analogous to that described in Example 2.

EXAMPLE 4

586 mg of sterile tert.-butanol, 75 mg of (95% pure) sodium 1,2-di-(9-cis-octadecenoyl)-3-sn-phosphatidyl-(S)-serine and 175 mg of (95% pure) 1-n-hexadecanoyl-2-(9-cis-octadecenoyl)-3-sn-phosphatidyl choline are dissolved in a round-bottomed flask, sterile-filtered over Acrodisc ($2.0 \times 10^{-7}$ m) and introduced into a sterile phial. The phial is rotated at 1750 rpm and the solvent is removed by blowing in a stream of purified nitrogen that has been filtered under a pressure of 1 bar. The phial is then evacuated under a high vacuum of $6.0 \times 10^{-2}$ mbar. The phial is sealed under an argon protecting-gas atmosphere.

Before use, 2.5 ml of sterile, calcium-free, phosphate-buffered (pH 7.2–7.4) saline solution (Dulbecco) containing doxorubicin in a concentration of 4 g/litre are added at room temperature, using a sterile syringe, to the film that has been manufactured, and the phial is shaken for ten minutes in a standardised laboratory shaking apparatus (Vortex, stage 6). The dispersion is then centrifuged for sixty minutes at 40 000 g. The filtrate is removed and the liposomes are suspended in 2.5 ml of 0.85% sterile saline solution.

EXAMPLE 5

506 mg of sterile tert.-butanol, 75 mg of (98% pure) sodium 1,2-di-(9-cis-octadecenoyl)-3-sn-phosphatidyl-(S)-serine (manufactured according to Browning J. and Seelig J., Chem. and Physics of Lipids 24 (1979) 103) and 175 mg of (99.5% pure) 1-n-hexadecanoyl-2-(9-cis-octadecenoyl)-3-sn-phosphatidyl choline (manufactured according to Eibl H., Chem. and Physics of Lipids 26 (1980) 239 and Eibl H., Angewandte Chemie 96 (1984) 247) are dissolved in a phial (15 ml). The solution is sterile-filtered over Acrodisc ($2.0 \times 10^{-7}$ m), introduced into a sterile phial and frozen at $-45°$. The phial is dried in vacuo until a temperature of 25° is reached and sealed under an argon atmosphere.

Before use, 2.5 ml of sterile, calcium-free, phosphate-buffered saline solution (Dulbecco) containing doxorubicin in a concentration of 4 g/litre are added to this dry preparation using a sterile syringe and the phial is shaken for one minute in a standardised laboratory shaking apparatus (Vortex, stage 6). After the addition of 22.5 ml of sterile, calcium-free, phosphate-buffered saline solution, which has been brought into equilibrium at 10°, the suspension is shaken for 2 minutes and then centrifuged for thirty minutes at 10 000 g and 10°. The residue is removed and the liposomes are resuspended in 25 ml of the sterile saline solution at 10°. The centrifuging process is repeated once the liposomes have been resuspended in 2.5 ml of 0.85% sterile saline solution. The liposome suspension contains 9 mg of doxorubicin per 250 mg of lipid and is suitable for i.v. administration.

EXAMPLE 6

In a manner analogous to that described in Example 5, doxorubicin-containing liposomes can be manufactured from a dry preparation containing 225 mg (0.297 mmol) of (99.5% pure) 1-n-hexadecanoyl-2-(9-cis-octadecenoyl)-3-sn-phosphatidyl choline and 25 mg (0.030 mmol) of (98% pure) sodium 1,2-di-(9-cis-octadecenoyl)-3-sn-phosphatidyl-S-serine. The liposome suspension contains 7 mg of doxorubicin per 250 mg of lipid and is suitable for i.v. administration.

EXAMPLE 7

A liposome dispersion can be manufactured in a manner analogous to that described in Examples 4 and 5 by dispersing a dry preparation of the phospholipids in 2.5 ml of sterile, calcium-free, phosphate-buffered (pH 7.2-7.4) saline solution (Dulbecco) containing mitomycin C in a concentration of 1 g/liter, centrifuging the dispersion and suspending the product in a saline solution.

EXAMPLE 8

A liposome dispersion can be manufactured in a manner analogous to that described in Example 5, but without centrifuging, by dispersing a dry preparation of the phospholipids in 2.5 ml of sterile, calcium-free, phosphate-buffered (pH 7.2-7.4) saline solution (Dulbecco) containing from fifty to two hundred micrograms of sodium N-acetyl-D-muramyl-L-alanyl-D-isoglutamine (British Patent Specification 1 570 625) and from one thousand to ten thousand units of recombinant human gamma-interferon isolated according to Patent Application 121.157 (Kyowa Hakko Kogyo Co.).

EXAMPLE 9

A liposome suspension can be manufactured in a manner analogous to that described in Example 5, but without the centrifuging, by dispersing a dry preparation of the phospholipids in 2.5 ml of sterile, calcium-free, phosphate-buffered (pH 7.2-7.4) saline solution (Dulbecco) containing from fifty to two hundred micrograms of sodium N-acetyldesmethyl-muramyl-L-alanyl-D-isoglutamine and from one thousand to one hundred thousand units of recombinant human gamma-interferon.

EXAMPLE 10

A liposome suspension can be manufactured in a manner analogous to that described in Example 4, but without the centrifuging process, by dispersing a dry preparation of the phospholipids in 2.5 ml of sterile, calcium-free, phosphate-buffered (pH 7.2-7.4) saline solution (Dulbecco) containing from fifty to two hundred micrograms of sodium N-acetyl-D-muramyl-L-alanyl-D-isoglutamine and from one thousand to one hundred thousand units of recombinant human gamma-interferon.

EXAMPLE 11

A liposome suspension can be manufactured in a manner analogous to that described in Example 4, but without the centrifuging, by dispersing a dry preparation of the phospholipids in 2.5 ml of sterile, calcium-free, phosphate-buffered (pH 7.2-7.4) saline solution (Dulbecco) containing approximately from fifty to two hundred micrograms of sodium N-acetyldesmethyl-muramyl-L-alanyl-D-isoglutamine and from one thousand to one hundred thousand units of recombinant human gamma-interferon.

EXAMPLE 12

To a round-bottomed flask containing 1 g of sorbitol (crystal size 125-500 μm) there are added dropwise, in vacuo, 14.2 ml of sterile tert.-butanol containing from 1 to 10 mg of N-acetylmuramyl-L-alanyl-D-isoglutaminyl-L-alanyl-2-(1,2-dipalmitoyl-sn -glycero-3-hydroxyphosphoryloxy)-ethylamide (manufactured according to European Patent Specification 25 495), 75 mg of sodium 1,2-di-(9-cis-octadecenoyl)-3-sn-phosphatidyl-(S)-serine and 175 mg of 1-n-hexadecanoyl-2-(9-cis-octadecenoyl)-3-sn-phosphatidyl choline. The solvent is then removed in vacuo under controlled temperature conditions. The resulting dry-powder preparation is sealed under an argon atmosphere.

Before use, 20 ml of distilled sterile water are added to this dry preparation at room temperature using a sterile syringe and the flask is shaken for ten minutes.

EXAMPLE 13

In a manner analogous to that described in Example 12, glucose, sucrose, lactose or sodium chloride may be used as the carrier instead of sorbitol.

We claim:

1. A pharmacuetical liposome composition comprising
   (a) synthetic, substantially pure sodium 1,2-di-(9-cis-octadecenoyl)-3-sn-phosphatidyl-(S)-serine,
   (b) synthetic, substantially pure 1-n-hexadecanoyl-2-(9-cis-octadecenoyl)-3-sn-phosphatidyl choline, and
   (c) a substance selected from the group consisting of antiphlogistics, antibiotics, antileishmaniasis agents, antimycotics, antineoplastics and immunomodulators, and a carrier liquid.

2. A pharmaceutical liposome composition according to claim 1 comprising
   (a) synthetic, substantially pure sodium 1,2-di-(9-cis-octadecenoyl)-3-sn-phosphatidyl-(S)-serine,
   (b) synthetic, substantially pure 1-hexadecanoyl-2-(9-cis-octadecenoyl)-3-sn-phosphatidyl choline, and
   (c) a substance selected from the group consisting of diclofenac, pirprofen, mitomycin, cytarabine, dactinomycin, daunorubicin, doxorubicin, etoposide, N-acetylmuramyl-L-alanyl-D-isoglutaminyl-L-alanine-2-(1,2-dipalmitoyl-sn-glycero-3-hydroxyphosphoryloxy)-ethylamide, the disodium salt of N-acetylmuramyl-L-alanyl-D-glutamic acid-$(C_\gamma)$-L-alanine-2-) 1,2-dipalmitoyl-sn-glycero-3-hydroxyphosphoryloxy)-ethylamide, the sodium salt of N-acetyldesmethylmuramyl-L-alanyl-D-isoglutamine, the sodium salt of N-acetyl-D-muramyl-L-alanyl-D-isoglutamine, N-acetyl-D-muramyl-L-alanyl-D-glutamine-α-n-butyl ester, $N^\alpha$-(N-acetyl-D-muramyl-L-alanyl-D-isoglutaminyl)-$N^\epsilon$-stearoyl-L-lysine, 6-0 stearoyl-N-acetylmuramyl-L-alanine-D-isoglutamine and lymphokines, and a carrier liquid buffered to pH 7.2-74.

3. A pharmaceutical liposome composition according to claim 1 comprising
   (a) synthetic, substantially pure sodium 1,2-di-(9-cis-octadecenoyl)-3-sn-phosphatidyl-(S)-serine,
   (b) synthetic, substantially pure 1-n-hexadecanoyl-2-(9-cis-octadecenoyl)-3-sn-phosphatidyl choline, and
   (c) a substance selected from the group consisting of mitomycin, cytarabine, dactinomycin, daunorubicin, doxorubicin, etoposide, N-acetylmuramyl-L-alanyl-D-isoglutaminyl-L-alanine-2-(1,2-dipalmitoyl-sn-glycero-3-hydroxyphosphoryloxy) -ethylamide, the sodium salt of N-acetyldesmethylmuramyl-L-alanyl-D-isoglutamine, the sodium salt of N-acetyl-D-muramyl-L-alanyl-D-isoglutamine, human gamma-interferon, interleukn 2, and mixtures of substances that are contained in culture filtrates obtained from cultures having human T-lymphocytes from the spleen or peripheral blood after stimulation by antigens or mitogens and that are characterised by a high content of macrophage-activating factor (MAF) and a carrier liquid buffered to pH 7.2–7.4.

4. A pharmaceutical liposome composition according to claim 1 comprising
   (a) synthetic, substantially pure sodium 1,2-di-(9-cis-octadecenoyl)-3-sn-phosphatidyl-(S)-serine,
   (b) synthetic, substantially pure 1-n-hexadecanoyl-2-(9-octadecenoyl)-3-sn-phosphatidyl choline,
   (c) a compound having immunomodulating action selected from the group consisting of N-acetylmuramyl-L-alanyl-D-isoglutaminyl-L-alanine-2-(1,2-dipalmitoyl-sn-glycero-3-hydroxyphosphoryloxy)-ethylamide, the sodium salt of N-acetyldesmethylmuramyl-L-alanyl-D-isoglutamine and the sodium salt of N-acetyl-D-muramyl-L-alanyl-D-isoglutamine and combinations thereof with mixtures of substances that are contained in culture filtrates obtained from cultures having human T-lymphocytes from the spleen or peripheral blood after stimulation by antigens or mitogens and that are characterised by at least a 70% content of MAF, and a carrier liquid buffered to pH 7.2–7.4.

5. A pharmeutical liposome composition according to claim 1 comprising
   (a) a synthetic, substantially pure sodium 1,2-di-(9-cis-octadecenoyl)-3-sn-phosphatidyl-(S)-serine,
   (b) synthetic, substantially pure 1-n-hexadecanoyl-2-(9-cis-octadecenoyl)-3-sn-phosphatidyl choline, and
   (c) N-acetylmuramyl-L-alanyl-D-isoglutaminyl-L-alanine-2-(1,2-dipalmitoyl-sn-glycero-3-hydroxyphosphoryloxy)-ethylamide.

6. A pharmaceutical liposome composition according to claim 1 comprising
   (a) synthetic, substantially pure sodium 1,2-di-(9-cis-octadecenoyl)-3-sn-phosphatidyl-(S)-serine,
   (b) synthetic, substantially pure 1-n-hexadecanoyl-2-(9-cis-octadecenoyl)-3-sn-phosphatidyl choline, and
   (c) recombinant human gamma interferon.

7. A pharmaceutical liposome composition according to claim 6 comprising
   (a) synthetic, substantially pure sodium 1,2-di-(9-cis-octadecenoyl)-3-sn-phosphatidyl-(S)-serine,
   (b) synthetic, substantially pure 1-n-hexadecanoyl-2-(9-cis-octadecenoyl)-3-sn-phosphatidyl choline, and
   (c) recombinant human gamma interferon having the following amino acid sequence;

H2N—Cys—Tyr—Cys—Gln—Asp—Pro—Tyr—Val—Gln—Glu—Ala—Glu—Asn—Leu—Lys—Lys—Tyr—Phe—Asn—Ala—Gly—His—Ser—Asp—Val—Ala—Asp—Asn—Gly—Thr—Leu—Phe—Leu—Gly—Ile—Leu—Lys—Asn—Trp—Lys—Glu—Glu—Ser—Asp—Arg—Lys—Ile—Met—Gln—Ser—Gln—Ile—Val—Ser—Phe—Tyr—Phe—Lys—Leu—Phe—Lys—Asn—Phe—Lys—Asp—Asp—Gln—Ser—Ile—Gln—Lys—Ser—Val—Glu—Thr—Ile—Lys—Glu—Asp—Met—Asn—Val—Lys—Phe—Phe—Asn—Ser—Asn—Lys—Lys—Lys—Arg—Asp—Asp—Phe—Glu—Lys—Leu—Thr—Asn—Tyr—Ser—Val—Thr—Asp—Leu—Asn—Val—Gln—Arg—Lys—Ala—Ile—His—Glu—Leu—Ile—Gln—Val—Met—Ala—Glu—Leu—Ser—Pro—Ala—Ala—Lys—Thr—Gly—Lys—Arg—Lys—Arg—Ser—Gln—Met—Leu—Phe—Arg—Gly—Arg—Arg—Ala—Ser—Gln—OH.

8. A pharmaceutical liposome composition according to claim 6 comprising
   (a) synthetic, substantially pure sodium 1,2-di-(9-cis-octadecenoyl)-3-sn-phosphatidyl-(S)-serine,
   (b) synthetic, substantially pure 1-n-hexadecanoyl-2-(9-cis-octadecenoyl)-3-sn-phosphatidyl choline, and
   (c) recombinant human gamma interferon having the following amino acid sequence;

H2N—Cys—Tyr—Cys—Gln—Asp—Pro—Tyr—Val—Lys—Glu—Ala—Glu—Asn—Leu—Lys—Lys—Tyr—Phe—Asn—Ala—Gly—His—Ser—Asp—Val—Ala—Asp—Asn—Gly—Thr—Leu—Phe—Leu—Gly—Ile—Leu—Lys—Asn—Trp—Lys—Glu—Glu—Ser—Asp—Arg—Lys—Ile—Met—Gln—Ser—Gln—Ile—Val—Ser—Phe—Tyr—Phe—Lys—Leu—Phe—Lys—Asn—Phe—Lys—Asp—Asp—Gln—Ser—Ile—Gln—Lys—Ser—Val—Glu—Thr—Ile—Lys—Glu—Asp—Met—Asn—Val—Lys—Phe—Phe—Asn—Ser—Asn—Lys—Lys—Lys—Arg—Asp—Asp—Phe—Glu—Lys—Leu—Thr—Asn—Tyr—Ser—Val—Thr—Asp—Leu—Asn—Val—Gln—Arg—Lys—Ala—Ile—His—Glu—Leu—Ile—Gln—Val—Met—Ala—Glu—Leu—Ser—Pro—Ala—Ala—Lys—Thr—Gly—Lys—Arg—Lys—Arg—Ser—Gln—Met—Leu—Phe—Arg—Gly—Arg—Arg—Ala—Ser—Gln—OH.

9. A pharmaceutical lyophilisate composition comprising
   (a) synthetic, substantially pure sodium 1,2-di-(9-cis-octadecenoyl)-3-sn-phosphatidyl-(S)-serine,
   (b) synthetic, substantially pure 1-n-hexadecanoyl-2-(9-cis-octadecenoyl)-3-sn-phosphatidyl choline, and
   (c) a substance selected from the group consisting of antiphlogistics, antibiotics, antileishmaniasis agents, antimycotics, antineoplastics and immunomodulators.

10. A pharmaceutical lyophilisate composition according to claim 9 comprising
    (a) synthetic, substantially pure sodium 1,2-di-(9-cis-octadecenoyl)-3-sn-phosphatidyl-(S)-serine,
    (b) synthetic, substantially pure 1-n-hexadecanoyl-2-(9-cis-octadecenoyl)-3-sn-phosphatidyl choline, and
    (c) N-acetylmuramyl-L-alanyl-D-isoglutaminyl-L-alanine-2-(1,2-dipalmitoyl-sn-glycero-3-hydroxyphosphoryloxy)-ethylamide.

* * * * *